United States Patent [19]

Kaufman

[11] Patent Number: 5,135,505
[45] Date of Patent: Aug. 4, 1992

[54] PROTECTIVE CATHETER DEVICE

[75] Inventor: Jerry M. Kaufman, Delray Beach, Fla.

[73] Assignee: Hemedix International, Inc., Delray Beach, Fla.

[21] Appl. No.: 685,817

[22] Filed: Apr. 15, 1991

[51] Int. Cl.⁵ .......................................... A61M 5/178
[52] U.S. Cl. ................................. 604/165; 604/198; 604/263
[58] Field of Search .............. 604/263, 198, 110, 135, 604/161-165, 167, 171; 128/919

[56] References Cited

U.S. PATENT DOCUMENTS

| | | | |
|---|---|---|---|
| 4,627,841 | 12/1986 | Dorr | 604/158 |
| 4,664,654 | 5/1987 | Strauss | 604/198 |
| 4,747,831 | 5/1988 | Kulli | 604/110 |
| 4,762,516 | 8/1988 | Luther et al. | 604/164 |
| 4,828,548 | 5/1989 | Walter | 604/164 |
| 4,846,805 | 7/1989 | Sitar | 604/165 |
| 4,850,961 | 7/1989 | Wanderer et al. | 604/53 |
| 4,917,669 | 4/1990 | Bonaldo | 604/164 |
| 4,944,728 | 7/1990 | Carrell et al. | 604/164 |
| 4,946,446 | 8/1990 | Vadher | 604/198 |
| 4,958,625 | 9/1990 | Bates et al. | 128/754 |
| 4,994,042 | 2/1991 | Vadher | 604/165 |
| 5,013,304 | 5/1991 | Russell et al. | 604/167 |
| 5,019,049 | 5/1991 | Haining | 604/165 |
| 5,030,205 | 7/1991 | Holdaway et al. | 604/164 |

Primary Examiner—C. Fred Rosenbaum
Assistant Examiner—Mark O. Polutta
Attorney, Agent, or Firm—Lerner, David, Littenberg, Krumholz & Mentlik

[57] ABSTRACT

Protective catheter devices are disclosed including a barrel for housing a catheter including a needle extending therefrom. The catheter is slidably retained within the barrel between a fully retracted position and an extended position, in which the needle can be inserted into a patient, and the device includes a locking mechanism for controlling the position of the needle within the barrel, which includes at least two positions; namely, a first position in which the needle is freely slidable within the barrel and a second position in which the needle is locked in its retracted position within the barrel, such that the needle cannot be displaced from its retracted position without repositioning the locking mechanism.

43 Claims, 10 Drawing Sheets

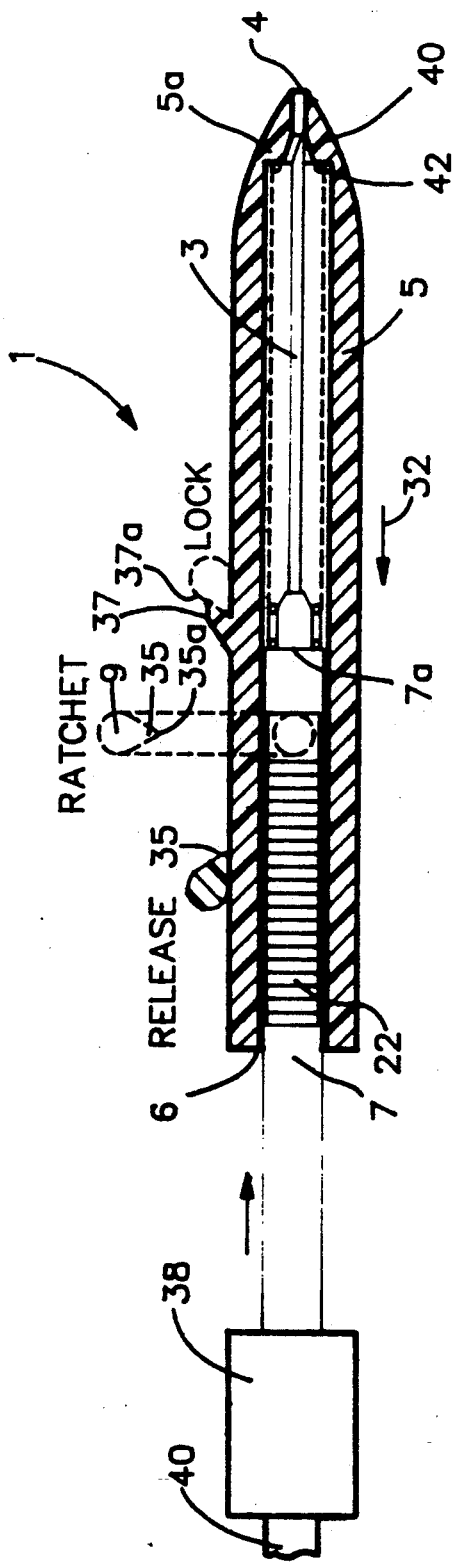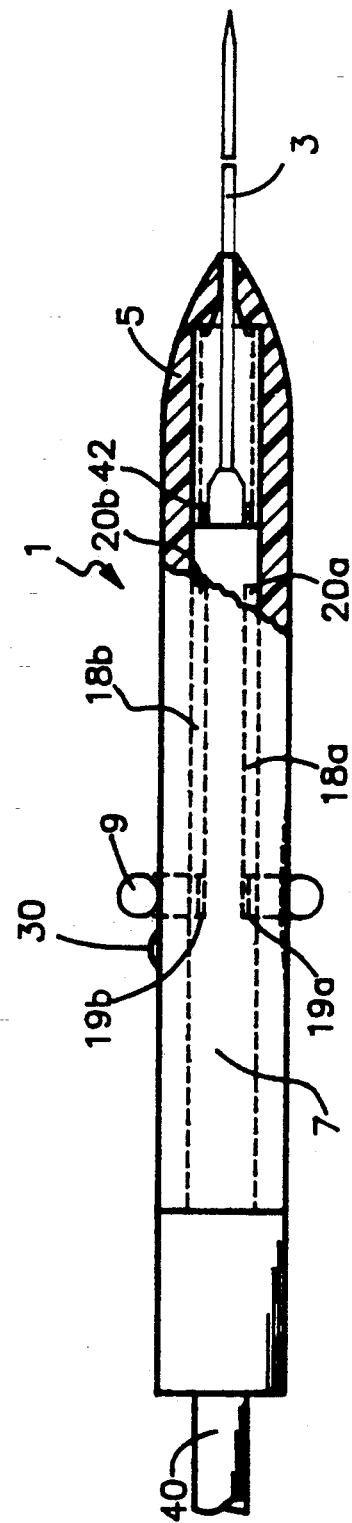

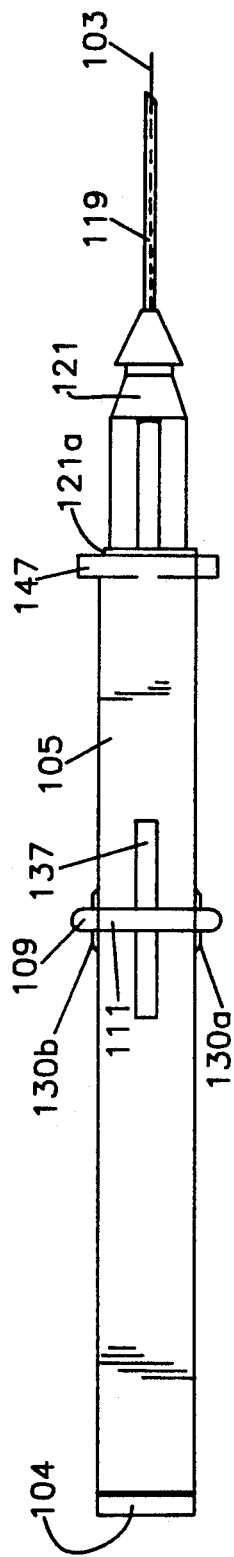
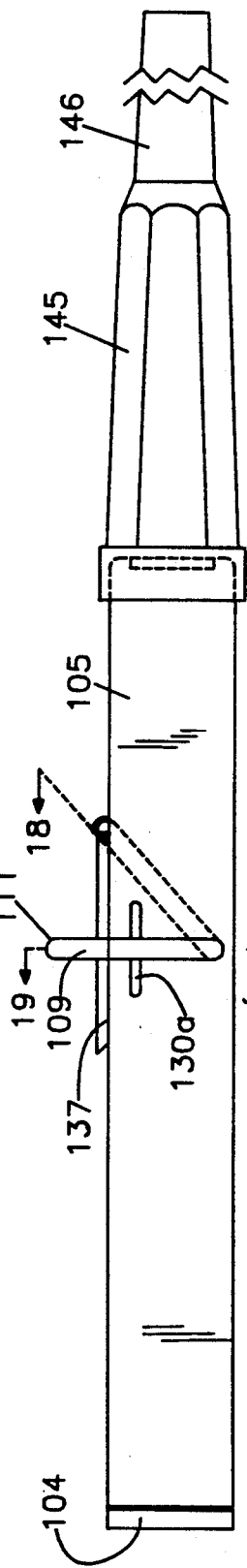
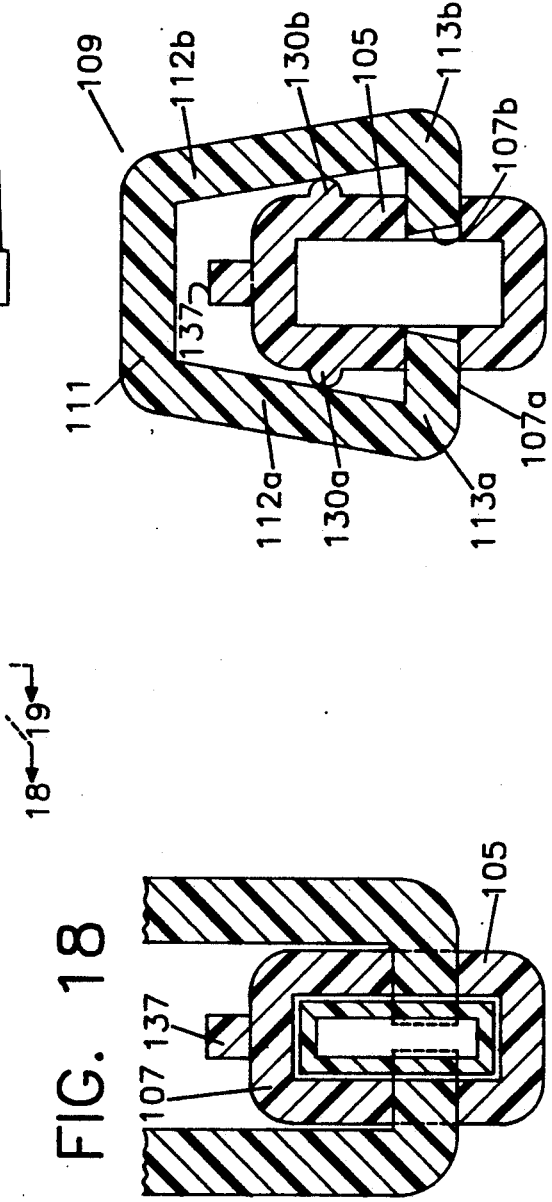

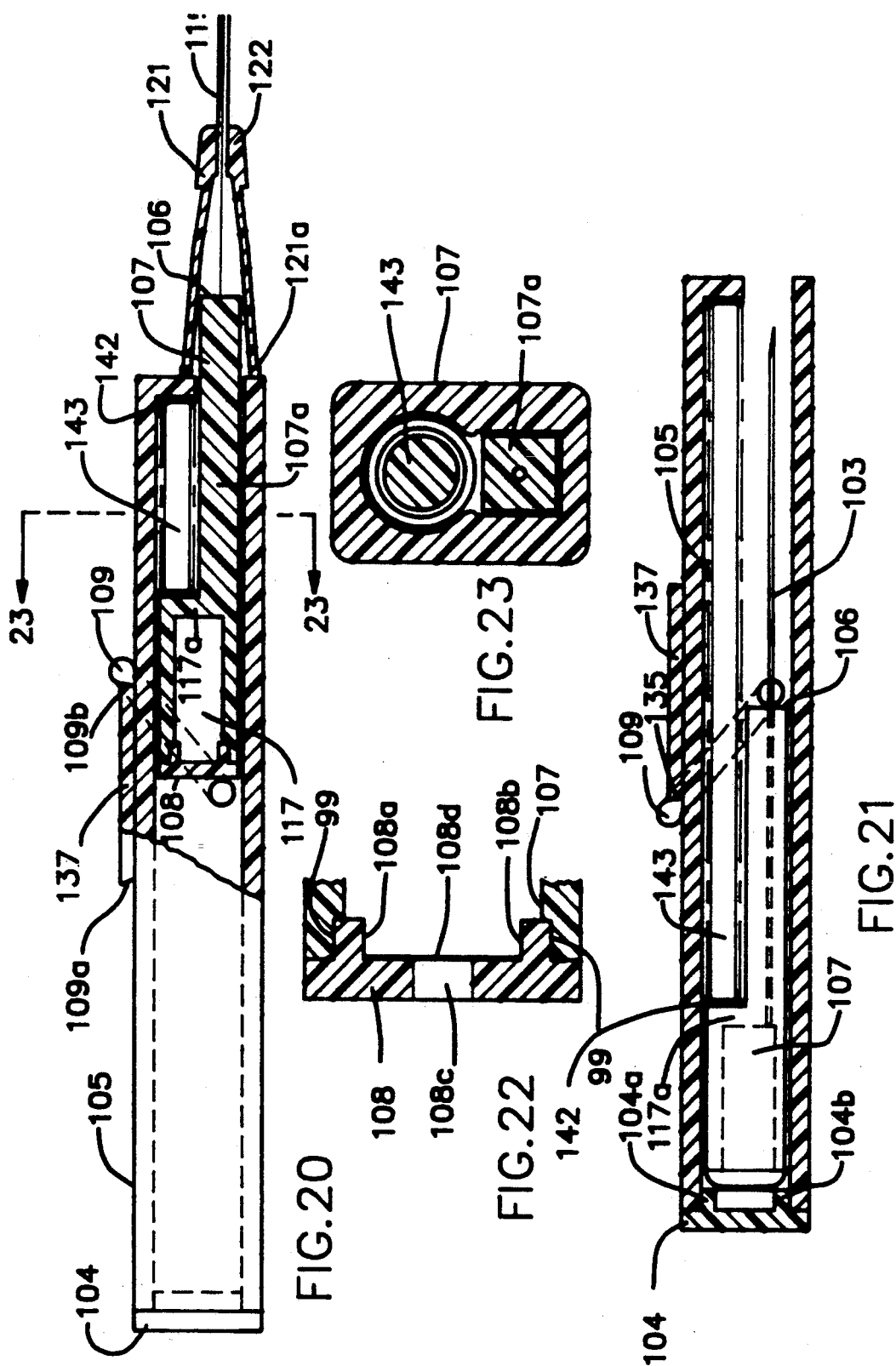

PROTECTIVE CATHETER DEVICE

FIELD OF THE INVENTION

The present invention relates to protective catheter devices. More particularly, the present invention relates to catheter devices which provide for the insertion of a needle and for the protection of the user thereof. Still more particularly, the present invention relates to such protective catheter devices of the angiocath type useful for the implantation of plastic cannulae. Still more particularly, the present invention also relates to IV catheter devices of various types.

BACKGROUND OF THE INVENTION

The number of devices which have recently been developed for use in connection with various catheters and which are specifically intended to prevent accidents from occurring upon removal of the needles employed therewith has grown dramatically. This has primarily been the result of concern among nurses and other medical personnel for the onset of infectious diseases, including the problem of AIDS, which has resulted from the handling of needles, catheters, cannulas and the like. Thus, the disease of AIDS and other such infectious diseases have been known to occur upon accidental pricking of such personnel from such needles after they have been removed from patients.

Reference to catheters throughout this application is intended to relate to the large number of variations of needle-containing devices of this type. These not only include intravenous catheters, which include a combination of elements for passing fluid to or from a fluid-carrying conduit or blood vessel in a patient, as well as angiocath-type devices, which employ a needle for the implantation of a plastic cannula or the like which can remain within the patient even after removal of the steel or other metallic needle used therewith.

Thus, in the case of the various intravenous-type catheters, a tubular conduit is generally employed with a connector at one end in order to connect the tubular conduit into a source of enteral fluid for delivery to the patient or to a reservoir for receiving fluid from the patient, and a second connector at the opposite end from the first connector which is fixedly or removably connectable to the needle.

On the other hand, in the case of angiocath-type devices, these can include a chamber for the removal of a small amount of bodily fluid or blood upon implantation, primarily to determine that the device is in proper working order and that the plastic cannula has been properly implanted, but which is then removed along with the needle so that the plastic cannula can serve various purposes, including subsequent use for the removal or insertion of fluids, etc.

In each of these cases, the problems of exposure to the needles, whether they are used solely for implantation of plastic cannulae or for intravenous applications themselves, have been considerable.

A recent significant advance in this field is represented by U.S. Pat. No. 4,966,589 and pending U.S. application Ser. No. 07/522,382 filed on May 11, 1990, to the present applicant, in which composite catheter assemblies are disclosed for this purpose. These include an embodiment in which, after removal, the needle can be readily withdrawn into a closed chamber so that it is no longer exposed and no longer presents a danger to medical personnel. In the devices shown in the '589 patent, retraction of a contaminated needle into the barrel is effected by depressing manual button 42 to release ratchet 36 and thus permit spring 28 to expand and move the carrier 26 to its retracted position within chamber 19.

While this device has thus provided a rather significant improvement in this field, the search has continued for additional improvements, and, in particular, for such protective catheter devices which include extension and retraction mechanisms with fixed positions for controlling the various placements of the needle itself within and without these devices.

SUMMARY OF THE INVENTION

In accordance with the present invention, these and other objects have now been realized by the invention of a protective catheter device which comprises needle means, barrel means for housing the needle means, with the needle means being slidably retained within the barrel means for slidable movement from a protected position entirely within the barrel means to an extended position with the needle means extending from the barrel means, whereby the needle means may be inserted into a patient, and positionable locking means for controlling that position of the needle means within the barrel means, the positionable locking means having at least two positions including a first position in which the needle means is freely slidable within the barrel means, and a second position in which the needle means is locked in the protected position within the barrel means whereby the needle means cannot be displaced from that protected position without repositioning the positionable locking means.

In accordance with a preferred embodiment of the protective catheter device of the present invention, the needle means includes a needle housing slidably disposed within the barrel member and a needle mounted on the needle housing and projecting therefrom. Preferably, the needle housing includes a fluid chamber for receiving fluid from the needle. In one embodiment the needle housing includes connection means for connecting the needle housing to a tubular conduit for the transport of fluid with respect to the needle housing.

In accordance with another embodiment of the protective catheter device of the present invention, biasing means are provided for biasing the needle means towards the protected position within the barrel means. Preferably, the needle means includes cooperative locking means for cooperating with the positionable locking means whereby when the positionable locking means is in the first position, the positionable locking means does not cooperate with the cooperative locking means, and when the positionable locking means is in the second position, the positionable locking means cooperates with the cooperative locking means to lock the needle means in the protected position.

In a preferred embodiment, the cooperative locking means comprises at least one transverse wall portion whereby when the positionable locking means is in the second position, the positionable locking means interacts with the at least one transverse wall portion. Most preferably the cooperative locking means comprises a pair of transverse wall portions whereby when the positionable locking means is in the second position, the positionable locking means can interact with either one of the pair of transverse wall portions.

In accordance with another embodiment of the protective catheter device of the present invention, the positionable locking means has a third position in which the needle means is locked in the extended position whereby the needle means cannot be displaced from the extended position without repositioning the positionable locking means.

In accordance with another embodiment of the protective catheter device of the present invention, when the positionable locking means is in the second position, the needle means can be locked in either the protected position or the extended position.

In accordance with another embodiment of the protective catheter device of the present invention, the positionable locking means has a third position in which the needle means is slidable from the protected position towards the extended position but is prevented from slidable movement from the extended position towards the protected position.

In accordance with a preferred embodiment of the protective catheter device of the present invention, the positionable locking means comprises pivotable handle means, and preferably includes projecting locking arm means, and the barrel means includes at least one aperture for the protecting locking arm means whereby the projecting locking arm means projects into the barrel means through the at least one aperture, and when the positionable locking means is in the first position, the projecting locking arm means does not engage the needle means, and when the positionable locking arm means is in the second position, the projecting locking arm means engages the needle means. Preferably, the needle means includes ratchet means and the projecting locking arm means includes pawl means for engaging the ratchet means when the positionable locking means is in the second position.

In a preferred embodiment, the positionable locking means has a third position in which the needle means is slidable from the protected position towards the extended position but is prevented from slidable movement from the extended position towards the protected position.

In a preferred embodiment, the ratchet means comprises a plurality of teeth, each of the plurality of teeth including a first surface and a second surface, the first surfaces of the plurality of teeth being substantially perpendicular to the needle means, and the second surfaces of the plurality of teeth being angularly disposed with respect to the needle means, and wherein the projecting locking arm means includes a first surface and a second surface and wherein the projecting locking arm means is rotatable when the positionable locking means is rotated between the first and second positions, whereby when the positionable locking means is in the second position, the first surface of the projecting locking arm means engages both the first and second surfaces of the ratchet means, and when the positionable locking means is in the third position, the second surface of the projecting locking arm means engages only the first surfaces of the plurality of teeth.

In accordance with another embodiment of the protective catheter device of the present invention, the barrel means includes urging means for urging the positionable locking means away from the at least one aperture when the positionable locking means is in the first position, so as to prevent the projecting locking arm means from engaging the needle means.

In a preferred embodiment of the protective catheter device of the present invention, the projecting arm means comprises a pair of projecting locking arms, and the barrel means includes a corresponding pair of apertures.

In accordance with a preferred embodiment of the protective catheter device of the present invention, implantable cannula means are provided mounted on the barrel means whereby when the needle means is in the extended position, the needle means projects through the implantable cannula means and the implantable cannula means may be implanted in the patient when the needle means is inserted into the patient. In a preferred embodiment, the implantable cannula means comprises plastic.

In accordance with a preferred embodiment of the protective catheter device of the present invention, the first and second positions of the positionable locking means are fixed first and second positions.

The nature of the present invention may be more fully appreciated with reference to the following detailed description, which in turn refers to the Figures as follows:

FIG. 1 is a side, elevational, partially sectional view of an intravenous catheter device in accordance with the present invention;

FIG. 2 is a side, elevational, partially sectional view of the catheter device shown in FIG. 1, with the needle extended from the barrel thereof;

FIG. 16 is a top, elevational view of an angiocath device in accordance with the present invention;

FIG. 17 is a side, elevational view of the angiocath device shown in FIG. 16 with a separate cover thereon;

FIG. 18 is a front, sectional view of the device shown in FIG. 17 taken along lines 18—18 thereof;

FIG. 19 is a side, sectional view of the angiocath device shown in FIG. 17 taken along lines 19—19 thereof;

FIG. 20 is a side, elevational, partially sectional view of the angiocath device shown in FIG. 16;

FIG. 21 is a side, elevational, sectional view of a portion of the angiocath device shown in FIG. 20, with the cannula removed therefrom;

FIG. 22 is a side, elevational, partial sectional view of a portion of the angiocath device shown in FIG. 20;

FIG. 23 is a front, sectional view of the angiocath device shown in FIG. 20 taken along lines 23—23 thereof;

DETAILED DESCRIPTION

Figure 3:
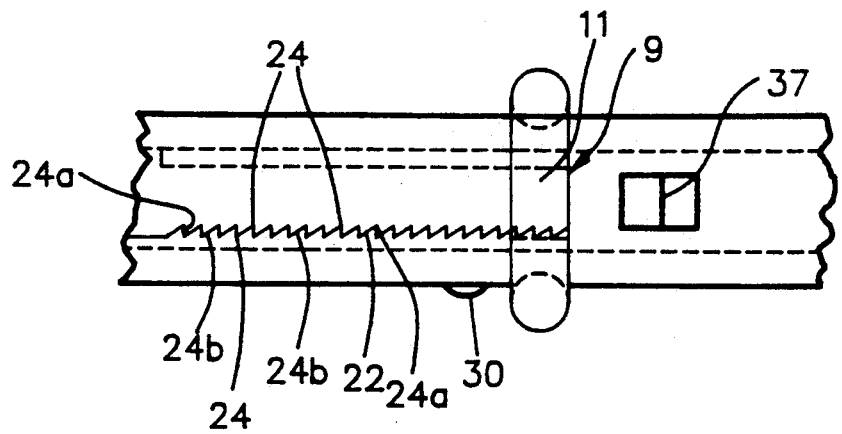
FIG. 3 is a partial, top, elevational view of a portion of the catheter device shown in FIG. 1.

The present invention can be more readily appreciated with reference to the foregoing Figures, in which like reference numerals refer to like portions thereof.

Referring first to FIG. 1, there is shown therein an intravenous catheter device which is intended for use by insertion of a needle 3 into a patient's vein or other fluid-carrying conduit in a patient. In this regard, use of the word "catheter" will include both the needle 3 and the catheter body 7 on which the needle 3 is mounted. The protective catheter device thus includes a protective barrel member 5 which slidably retains the catheter, such that the needle and catheter body are slidably movable between a retracted position as shown in FIG. 1, and an extended position as shown in FIG. 2. The needle itself is a conventional hollow metal needle used for intravenous and other such purposes. When the catheter is in the retracted position shown in FIG. 1, the tip of the needle 3 is fully retained within the protective barrel member 5, so that it cannot inadvertently contact medical workers or the like.

The principal object of the protective catheter device of the present invention is to control the position of the catheter with respect to the barrel member 5 between various positions from the retracted position to the extended position shown in the Figures. As for the protective barrel member 5 itself, it is a longitudinally extending, elongated, cylindrical member, which includes a circular opening 6 at its end distal from the needle 3, and a nose portion 5a, which is generally conical in configuration, and includes a central aperture 4, which can readily accommodate the needle 3 for extension therethrough.

Figure 4:
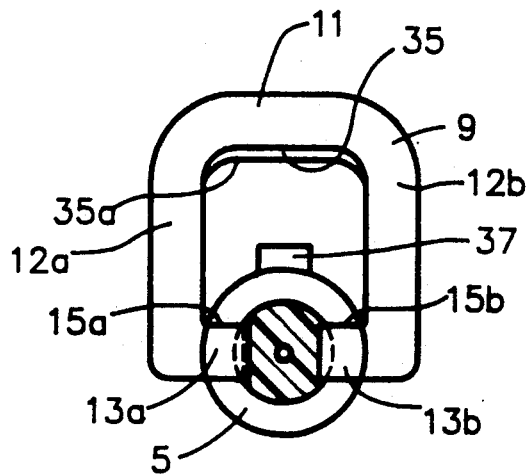
FIG. 4 is a front, elevational, partially sectional view of the catheter device shown in FIG. 1.

In accordance with the embodiment of the invention shown in FIGS. 1 and 2, control of the position of the catheter is effected by means of handle 9. Handle 9, as can best be seen in FIG. 4, includes a gripping member 11, two depending arms 12a and 12b, and two inwardly projecting elbows 13a and 13b, respectively. Handle 9 is thus pivotable about these inwardly projecting elbow portions 13a and 13b, which, in turn, project through the wall of the barrel member 5, and particularly through a pair of respective apertures, 15a and 15b, therethrough, which correspond to inwardly projecting elbows 13a and 13b, respectively. In this manner, the handle 9 can pivotably rotate about an axis passing through the center of both inwardly projecting elbows 13a and 13b. Both of these inwardly projecting elbows 13a and 13b, thus project inwardly beyond the inner wall of the barrel member 5 into the interior thereof. However, the outer surface of the catheter body 7 accommodates these inwardly projecting elbows 13a and 13b by the presence of longitudinally extending grooves 18a and 18b therein, as can best be seen in FIG. 2. These longitudinally extending grooves 18a and 18b extend along the respective opposite side walls of the catheter body 7 for a predetermined distance between end walls 19a and 20a, on the one hand, and end walls 19b and 20b, on the other. Thus, the length of these longitudinally extending grooves 18a and 18b, or the distance between the respective end walls 19a and 20a, on the one hand, and end walls 19b and 20b, on the other, will determine the extent of possible travel of the catheter body 7 within the barrel member 5; i.e., from the fully retracted position shown in FIG. 1, in which the inwardly projecting elbows 13a and 13b come into contact with end walls 20a and 20b, and the fully extended position shown in FIG. 2, in which the inwardly projecting elbows 13a and 13b come into contact with the opposite end walls 19a and 19b, respectively. The depth of longitudinally extending grooves 18a and 18b must therefore be sufficient to accommodate as much of the inner ends of inwardly projecting elbows 13a and 13b as project within the barrel member 5 beyond the surface of the inner walls thereof.

In the embodiment shown in FIGS. 1 and 2, within at least one of the longitudinally extending grooves 18a and 18b, in this case longitudinally extending groove 18a, there is contained a ratchet surface 22, which can best be seen in FIGS. 1 and 3. The ratchet surface 22 itself includes a plurality of teeth 24, each of these teeth including a substantially 10 vertical surface 24a and an angularly disposed surface 24b. Ratchet 22 is intended to cooperate with the inner face 29 of inwardly projecting elbow 13a, which is most readily seen in FIGS. 7 and 8.

The details concerning operation of handle 9 can be readily appreciated with reference to various aspects of FIGS. 1-14. It should thus be borne in mind that, as handle 9 is manually moved between the three principal positions shown in FIG. 1, the face of inwardly projecting elbow 13a will rotate about the pivot point represented by the central axis of inwardly projecting elbow 13a and about which handle 9 rotates.

When handle 9 is thus in the position extending rearwardly with respect to barrel member 5, and thus in the position indicated as the "release" position in FIG. 1, depending arm 12a of handle 9 will come into contact with elevated member 30, which projects from the outer surface of the barrel member 5, as can best be seen in FIG. 3. This, in turn, will urge the inwardly projecting elbow 13a outwardly with respect to the barrel member 5, i.e., away from the catheter body 7, and from ratchet portion 22 within longitudinally extending groove 18a thereof. In this manner, the inner face 29 of inwardly projecting elbow 13a will move towards the aperture 15a in the barrel member 5, and away from the surface of ratchet member 22 within the longitudinally extending groove 18a. Thus, in this release position, there will be no interfering contact between either inwardly projecting elbow 13a or 13b, at least between the ends of groove 18a and 18b, respectively, and the catheter itself can be freely, slidably moved, such as from the fully retracted position of FIG. 1 to the fully extended position of FIG. 2.

By rotating the handle member 9 in a clockwise direction from the above-discussed release position to the central "ratchet" position shown in FIG. 1, it can be seen that the arm portion 12a of handle 9 is now displaced from it prior contact with raised portion 30, thus permitting the inward end of inwardly projecting elbow 13a to move towards the ratchet 22. In addition, the inner face 29 of the inwardly projecting elbow 13a will undergo a one-quarter rotation about the rotational axis of handle 9.

Figure 8:
FIG. 8 is a top, elevational view of the portion of the handle means shown in FIG. 7 taken along lines 8—8 thereof.
Figures 5, 6, 7:
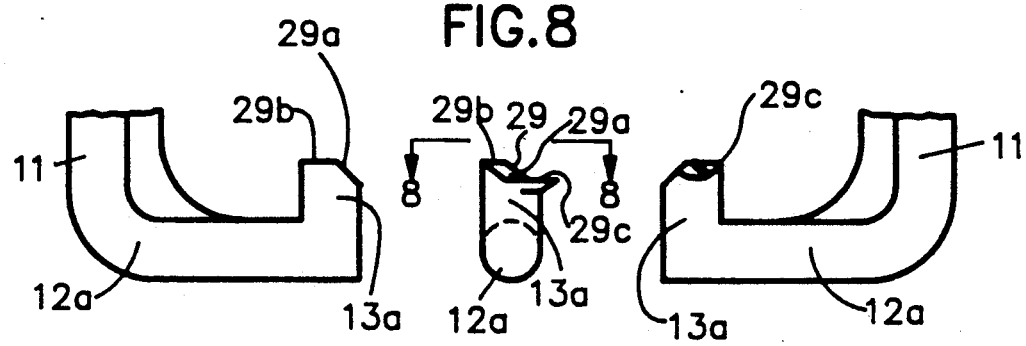
FIG. 5 is a partial, broken view of a portion of the handle means of the catheter device shown in FIG. 4.
FIG. 6 is another partial, broken, elevational view of the handle means of the catheter device shown in FIG. 4.
FIG. 7 is a partial, elevational view of a portion of the handle means shown in FIG. 5.
Figure 9:
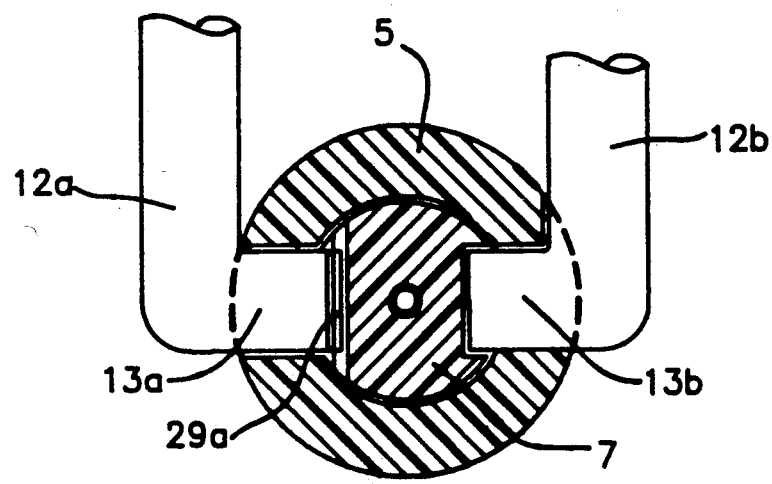
FIG. 9 is a front, partially sectional view of the catheter device shown in FIG. 1 in the release position.
Figure 10:
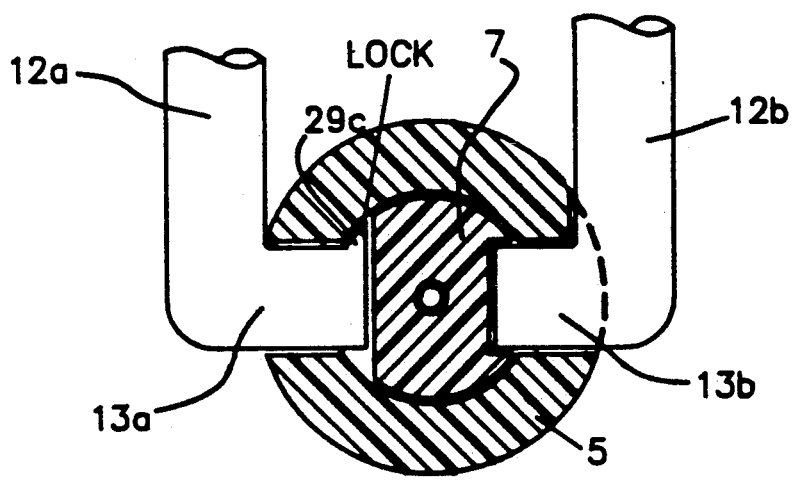
FIG. 10 is a front, partially sectional view of the catheter device shown in FIG. 1 in the locked position.
Figure 11:
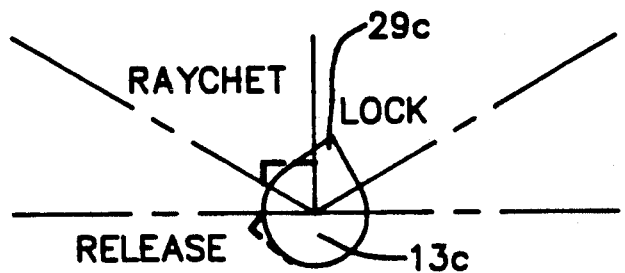
FIG. 11 is a schematic representation of the locking mechanism of the catheter device shown in FIG. 1 in the release, ratchet and locked positions thereof.
Figure 12:
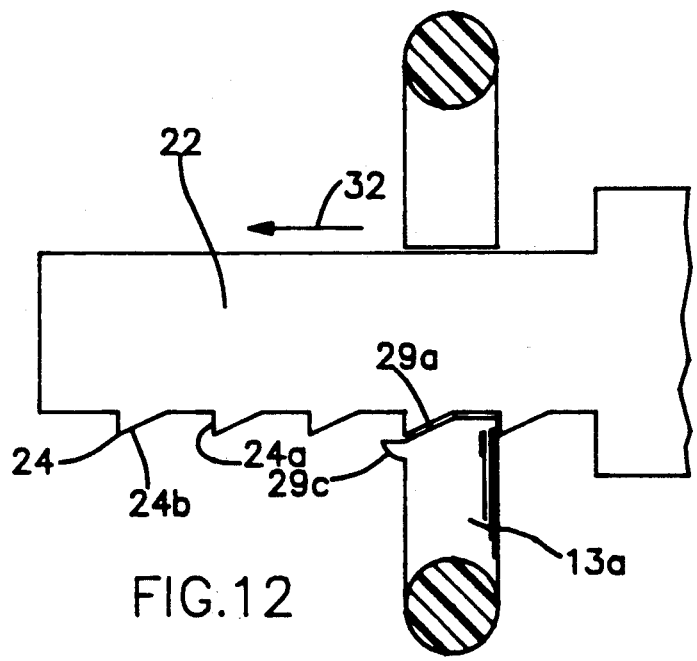
FIG. 12 is a partial representational view of the operation of the locking mechanism of the catheter shown in FIG. 1 in the locked position.
Figure 13:
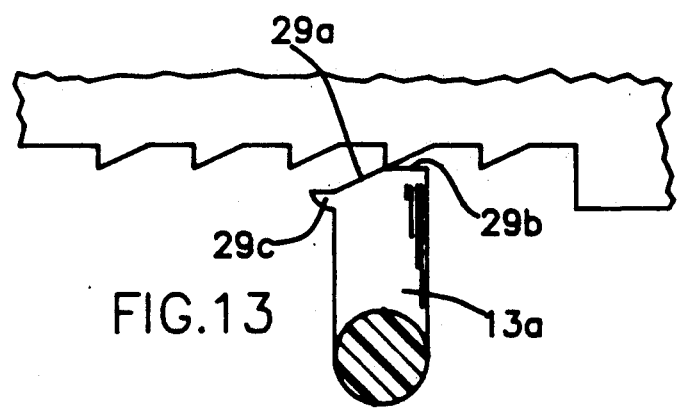
FIG. 13 is a partial representational view of the locking mechanism of the catheter shown in FIG. 12 in the release position.
Figure 14:
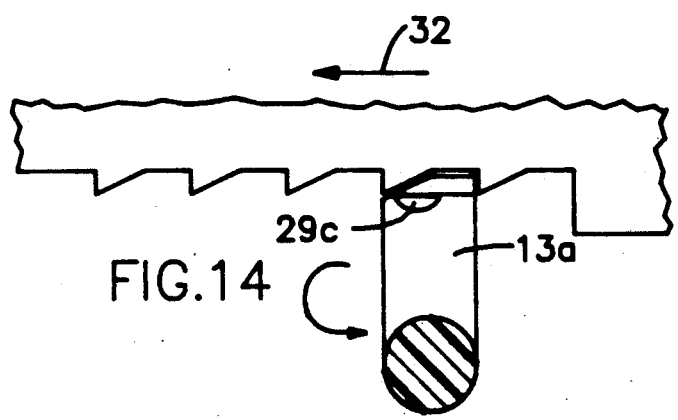
FIG. 14 is a partial representational view of the locking mechanism of the catheter shown in FIG. 12 in the ratchet position.

Turning to FIGS. 7 and 8, it can be seen that the inner face 29 of inwardly projecting elbow 13a is shown in more detail. In particular, inner face 29 includes an angled face 29a and a horizontal face 29b, with the angled face 29a including a projecting portion 29c extending therefrom Thus, when the handle member 9 is in the ratchet or central position shown in FIG. 1, the extending portion 29c extends in a direction substantially parallel to the ratchet 22 itself in the manner shown in FIG. 12, again with the arm portion 12a free of the raised portion 30, thus permitting the inner face 29 of the inwardly projecting elbow 13a to enter the teeth of the ratchet 22 in the manner shown in FIGS. 9 and 12. In particular, the horizontal face 24b can now enter the portion between the individual teeth, abutting against vertical portion 24a of teeth 24, while the angled face 29a can correspond with ramp portion 24b of the teeth 24 in ratchet 22. In this manner, the inwardly projecting elbow 13a prevents any movement of the catheter body 7 in the direction represented by arrow 32 in FIGS. 1 and 12, i.e., in a direction which will permit return of the catheter body 7 into the barrel member 5 or into the retracted position therein.

On the other hand, the catheter can be moved in the direction from the retracted position shown in FIG. 1 towards the extended position shown in FIG. 3 even when the handle member 9 is in this central or ratchet position, by means of the inner face 29 of inwardly projecting elbow 13a merely sliding over ramp portions 24b of the teeth 24 in ratchet 22.

By further rotation of the handle 9 in the clockwise direction shown in FIG. 1, into the locked position, the location of the catheter body 7 with respect to the barrel member 5, and the corresponding location of needle 3, can now be locked into position. This is accomplished because further rotation of the inner face 29 of inwardly projecting elbow 13a another one-quarter turn about the axis of rotation of the handle 9 causes the projecting portion 29c to now rotate into a position substantially perpendicular to the direction of the teeth 24 of ratchet 22, or into the position shown in FIGS. 10 and 14. In this position, the projecting portion 29c now blocks movement of the ratchet 22 in either direction, including in a direction opposite to that of arrow 32, by abutting against the vertical portion 24a between the individual teeth 24, and against the bottom of ramp 24b thereof.

Referring again to FIGS. 1 and 4, it can also be seen that the inner surface of gripping member 11 of handle 9 includes a projecting portion 35, which projects inwardly therefrom, and includes a depending lip 35a. This depending lip 35a can then coact with a locking member 37, which is disposed on the outer surface of the barrel member 5. This locking member 37 thus includes an angularly disposed projecting lip 37a, which is preferably resilient, and thus by rotation of the handle 9 in the clockwise direction shown in FIG. 1 into the locked position, the handle 9 can be fixed in that fully locked position by mean of depending lip 35a snap-fitting over the projecting lip 37a of locking member 37. This will retain the handle 9 in the locked position until it is forcibly removed by a reverse action; i.e., by snapping depending lip 35a over the projecting lip 37a and forcing the handle 9 in a counterclockwise direction as shown in FIG. 1.

It also should be noted that the rearward portion of the catheter body 7 includes conventional means such as a Luer clip 38 which permits one to attach the inner hollow portion of catheter body 7 with conventional tubing 40, which can then extend to either carry blood from the catheter body 7, or for intravenous transfusion or the like.

It is next noted that within the nose portion 5a of the barrel member 5, the inner surface of the barrel member 5 includes an annular front end wall 40, surrounding central aperture 4. Within the inner chamber of barrel member 5, a resilient spring member 42 can thus be retained between the front wall member 40 and the front wall 7a of the catheter body 7 surrounding the needle 3. This spring member 42 thus tends to resiliently urge the catheter body 7 towards the fully retracted position shown in FIG. 1 and out of the extended position shown in FIG. 2.

In this manner, when the catheter hereof is in the fully extended configuration shown in FIG. 2, when the handle member 9 is rotated in a counter-clockwise direction from the locked position to the release position, the inner face 29 of the inwardly projecting elbow 13a is disengaged from the ratchet member 22 of the catheter body 7, by means of raised portion 30 engaging the inner face of depending arm 12a and urging it away from the surface of barrel member 5. The spring member 42 is thus free to urge the catheter body 7, preferably by a "snap-action" thereagainst, into the fully retracted position shown in FIG. 1, thus withdrawing the needle 3 and eliminating any possible subsequent inadvertent contact with the needle 3, such as by medical personnel. Indeed, this mechanism can itself be used to withdraw the needle 3 from the patient's arm or other body-fluid-carrying conduit so that the needle 3 is never exposed for potential inadvertent contact, not even for the instant subsequent to withdrawal thereof.

Figure 15:
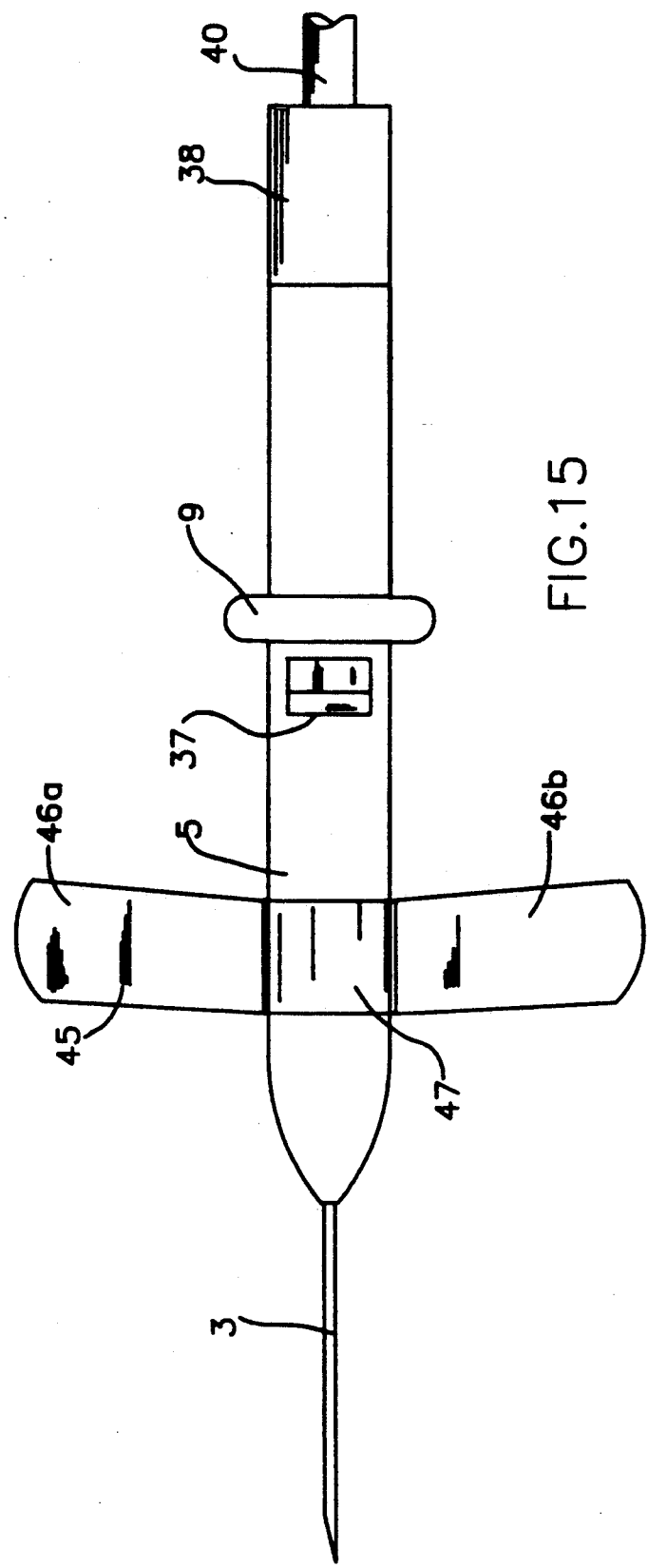
FIG. 15 is top, elevational view of another embodiment of a protective catheter device in accordance with the present invention.

The modified embodiment of the catheter device shown in FIG. 1 which is shown in FIG. 15 includes corresponding parts, except that in this case it also includes a wing member 45 which is affixed to the forward portion of the barrel member 5 by means of a circular collar 47 surrounding same. The wing member 45 includes a pair of wings 46a and 46b, which are conventional butterfly-type wings which can be employed to affix the catheter itself to the patient by affixing it to the skin. The butterfly member 40 also assists in manipulation of the catheter device itself and in the handling of same. This butterfly member is preferably made of thermoplastic compositions, such as polyethylene, or thermoplastic elastomers.

Turning next to FIGS. 16 and 17, another embodiment of the present invention is shown, in this case relating to an angiocath device primarily for use in the implantation of a plastic cannula which is intended to remain in a patient for extended periods of time.

Referring to FIGS. 16, 17 and 20, in this device a hollow needle 103 is connected to a catheter body 107.

Catheter body 107 is slidably disposed within the barrel member 105. In this manner, the catheter body 107, as well as needle 103, can be slidably moved from the extended position shown in FIG. 20 to the fully retracted position shown in FIG. 21.

In the case of this angiocath device, the corresponding locking mechanism operates as follows: The handle member 109 includes a gripping portion 111, and a pair of depending arms 112a and 112b, as can best be seen in FIG. 19, which terminate in inwardly projecting elbows 113a and 113b. Each of these inwardly projecting elbows 113a and 113b extends through corresponding apertures 107a and 107b, which extend through the side walls of the barrel member 107. Thus, the handle member 109 is pivotable about the central axis of these inwardly projecting elbows 113a and 113b in the manner shown in FIG. 17. The handle member 109 shown in this embodiment basically has two different configurations; namely, a release configuration and a locked configuration, although in this mode there are two different locked configurations, either frontwardly or rearwardly directed.

With handle 109 in its central position as shown in FIG. 17, the handle 109 is in the release position, as also shown in FIG. 19. In this configuration, the depending arms 112a and 112b of the handle member 109 bear against corresponding raised surfaces 130a and 130b which project from the side walls of the barrel member 105, thus urging each of the depending arms 112a and 112b outwardly, and, in turn, resulting in the inwardly projecting elbows 113a and 113b being withdrawn into apertures 107a and 107b, such that they no longer project beyond the inner wall of the barrel member 5 into the interior thereof. In this configuration it can thus be seen that, with neither inwardly projecting elbow projecting into the area where the catheter body 107 is slidably disposed, there is nothing to interfere with slidable movement of the catheter body 107 within the entire extent of the inner area of barrel member 105.

On the other hand, when the handle 109 is shifted either forwardly (clockwise) into the phantom position shown in FIG. 17, or rearwardly (counterclockwise) from the central position shown in FIG. 17, the depending arms 112a and 112b no longer impinge upon the raised portions 130a and 130b, thus permitting the inwardly projecting elbows 113a and 113b to extend inwardly into the interior of the barrel member 105 into the configuration shown in FIG. 18. This is only possible, however, when the catheter body 107 is not at a location which blocks apertures 107a and 107b. Thus, the handle 109 can only be placed in the locked position when the catheter body 107 is either in the position shown in FIG. 20 or that shown in FIG. 21; namely, either fully in its extended position, as shown in FIG. 20, or fully in its retracted position, as shown in FIG. 21.

In the fully extended position of FIG. 20, the inwardly projecting elbows 113a and 113b of handle 109 can extend inwardly into the inner portion of the barrel member 105, and thus block rearward movement of the catheter body 107 by abutting against the rear wall 108 of the catheter body 107, thus preventing slidable movement from the fully extended position shown in FIG. 20 to the retracted position of FIG. 21.

Similarly, when the catheter body 107 is in the fully retracted position shown in FIG. 21, and the handle member 109 is locked, as in the position shown in FIG. 21, the inwardly projecting elbows 113a and 113b can again extend inwardly into the inner portion of the barrel member 105, and in this condition prevent forward movement of the catheter body 107 by abutting against the front wall 106 of the catheter body 107, thus preventing forward slidable movement of the catheter body 107 from the fully retracted position shown in FIG. 21 towards the fully extended position shown in FIG. 20.

The barrel member 105 is closed off in its rearward direction by closure member 104 whose configuration can best be seen in FIG. 21. Closure member 104 thus includes two depending lips 104a and 104b whose outer dimension matches the inner dimension of barrel member 105, for snap-fit engagement therewith. Closure member 104 can be permanently glued in place, or it can be removable, thus permitting subsequent removal of the catheter body 107 from the barrel member rearwardly therefrom, if necessary The barrel member 105 also includes a locking member 137 on its surface below the handle 109. This locking member includes two angularly disposed projecting lips 109a and 109b, which, acting in concert with the depending lip portion 135a of the projecting portion 135 of the handle member 109, permits the handle member 109 to be locked in either of the two locked positions, either forward or rearward, as shown in FIGS. 20 and 21, respectively. By thus rotating the handle member 109 either counterclockwise from the position shown in FIG. 20 or clockwise from the position shown in FIG. 21, the handle member 109 can be snapped out of these locked positions and rotated into the release position shown in FIGS. 17 and 19.

The rear face of catheter body 107 includes a rear wall portion 108. This rear wall portion portion 108 can be more clearly seen in FIG. 22, and includes two depending lip members 108a and 108b which can be affixed to the walls of the catheter body 107, or which can fit into a groove 99 therein. The center of wall portion 108 includes an aperture 108c, which is sealed by a membrane 108d extending thereacross. This membrane 108d is intended to permit air within the inner chamber 117 of the catheter body 107 to exit therefrom, while, at the same time, preventing any liquid therein from passing therethrough. This membrane 108d seals off central opening 117 into which the distal end of hollow needle 103 enters. Thus, blood or other fluid entering needle 103 can flow into the aperture 117 within the catheter body 107 and fill same. The presence of membrane 108d permits this to occur by permitting air to exit through the membrane 108d so that the liquid enters cavity 117.

In the configuration of this catheter device as is shown in FIGS. 16 and 20, the needle 103 is partially surrounded by a plastic cannula 119. In the embodiment shown, this plastic cannula 119 is produced from flexible plastic such as Teflon, or from silicone rubber and the like, and includes an elongated cylindrical section which covers a substantial portion of needle 103, but whose cylindrical end portion terminates a short distance from the tip of needle 103. In this manner, needle 103 can be used to insert the cannula 119 into the patient simultaneously with the needle 103. In the embodiment shown, however, the distal end of the plastic cannula 119, to which the elongated cylindrical section is attached, includes a cover portion 121 extending therefrom. Cover portion 121 has an essentially conical configuration, the inner end 121a thereof surrounding the opening into the interior of barrel member 105. The forward end of cover portion 121 includes a collar portion 122, which leads to the elongated cylindrical portion of cannula 119, which is intended to enter the patient. Thus, needle 103 can be inserted along with plastic cannula 119. Upon subsequent removal of needle 103, the plastic cannula 119, including attached cover portion 121, will remain in the patient. This can be more particularly seen in FIG. 25, and will be discussed in more detail below.

Forward of the reservoir 117 in the catheter body 107, there is a reduced diameter portion 107a of catheter body 107. In this manner, between the wall portion 117a of the rear expanded portion of the catheter body 107 forming chamber 117, and the inner face of front wall portion 105a of the barrel member 105, an elongated, resilient, coiled spring member 142 is located. This spring member 142 is in its compressed state as shown in FIG. 20, and is compressed between these two wall portions 105a and 117a, thus exerting considerable force which tends to urge the catheter body 107 rearwardly. However, because of the location of handle 109 in the locked position shown in FIG. 20, such that inwardly projecting elbows 113a and 113b are projecting inwardly into the inner surface of the barrel member 105, so as to block rear wall 108 thereof, the catheter 107 remains in its fully extended position.

An inner guide bar 143 is located within the coiled spring 142 and is affixed to the wall member 117a of the catheter body 107, preferably by glue or the like. The purpose of guide bar 143 is to maintain the coiled spring 142 in an essentially cylindrical configuration around the guide bar 143 so that it can exert appropriate force when the handle 109 is released from its locked position. Thus, when the handle 109 has been released from its locked position, and when the catheter body 107 is moved into its retracted position, such as shown in FIG. 21, the guide bar 143 remains affixed to the wall portion 117a of the catheter body 107 and projects therefrom. In this embodiment, however, with the spring member 142 in its fully extended position, there is no need for a guide bar along its entire length to prevent it form maintaining a cylindrical configuration.

Since prior to use the angiocath device of FIGS. 16 et seq. is in its fully extended position as shown in FIGS. 16 and 20, in order to protect medical personnel and the like prior to use, a cap member 145, as shown in FIG. 17 is employed. This cap member 145 includes a forward extended portion 146 covering the full extent of the needle 103 and the plastic cannula 119, and clamping over the rim 147 at the front portion of the barrel means 105 to again fully cover both the needle 103 and the plastic cannula 119. Upon removal of cover 145, the device is ready for use in the configuration shown in FIGS. 16 and 20.

Figure 24:
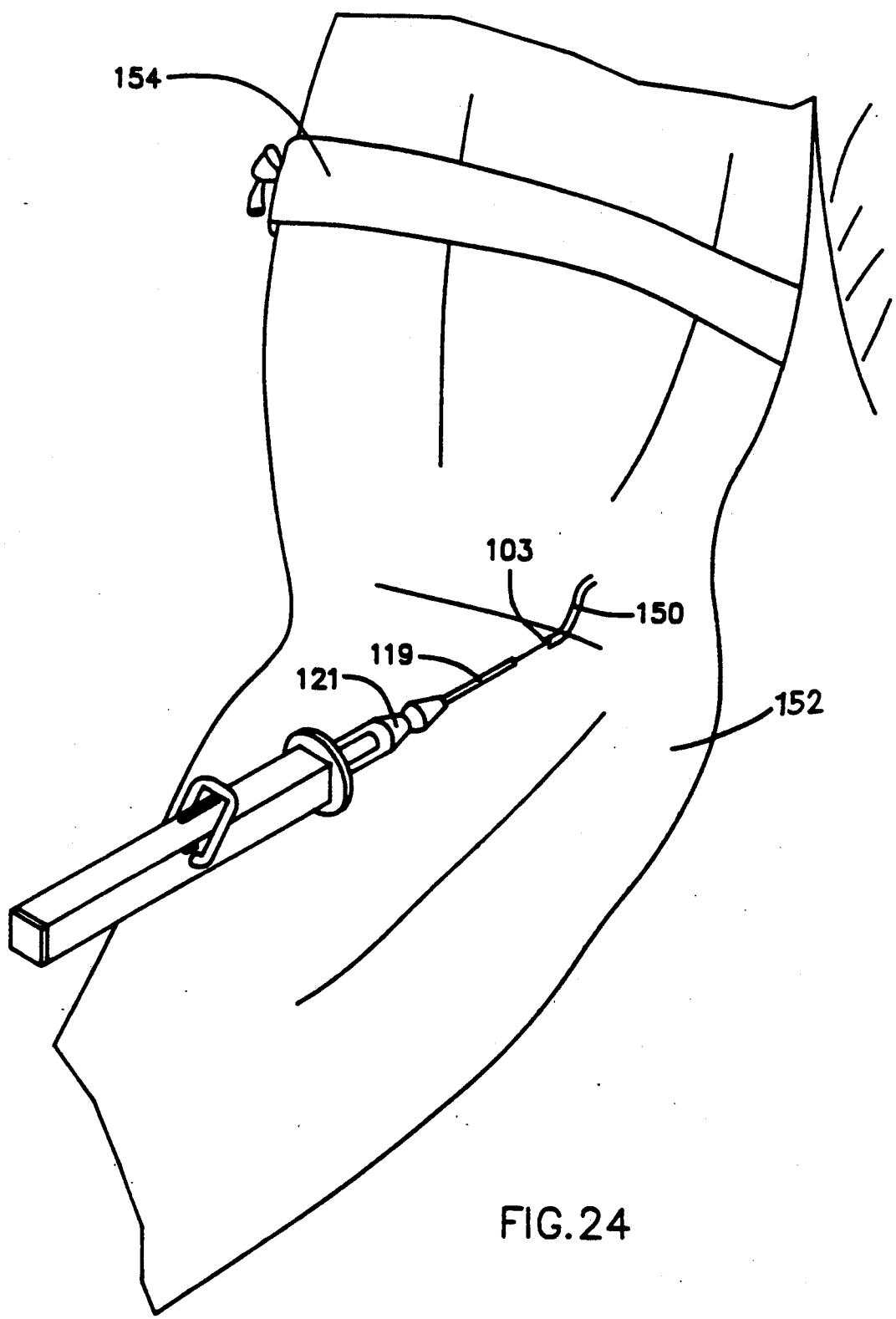
FIG. 24 is a top, perspective view of an angiocath device such as that shown in FIG. 16 during use in accordance with the present invention.
Figure 25:
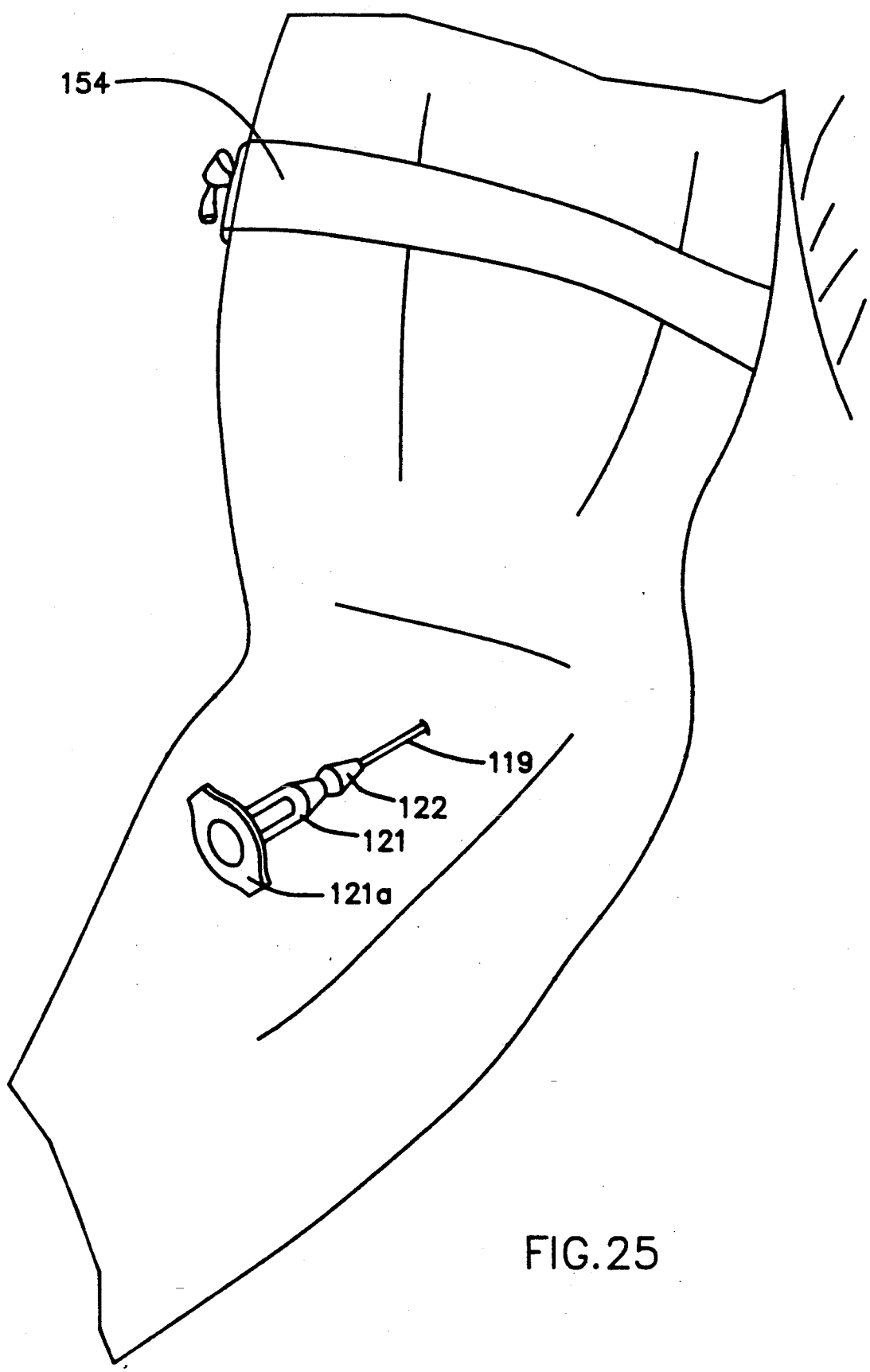
FIG. 25 is a top, perspective view of an implanted cannula implanted in accordance with the angiocath device shown in FIG. 16 after removal of the catheter.
Figure 26:
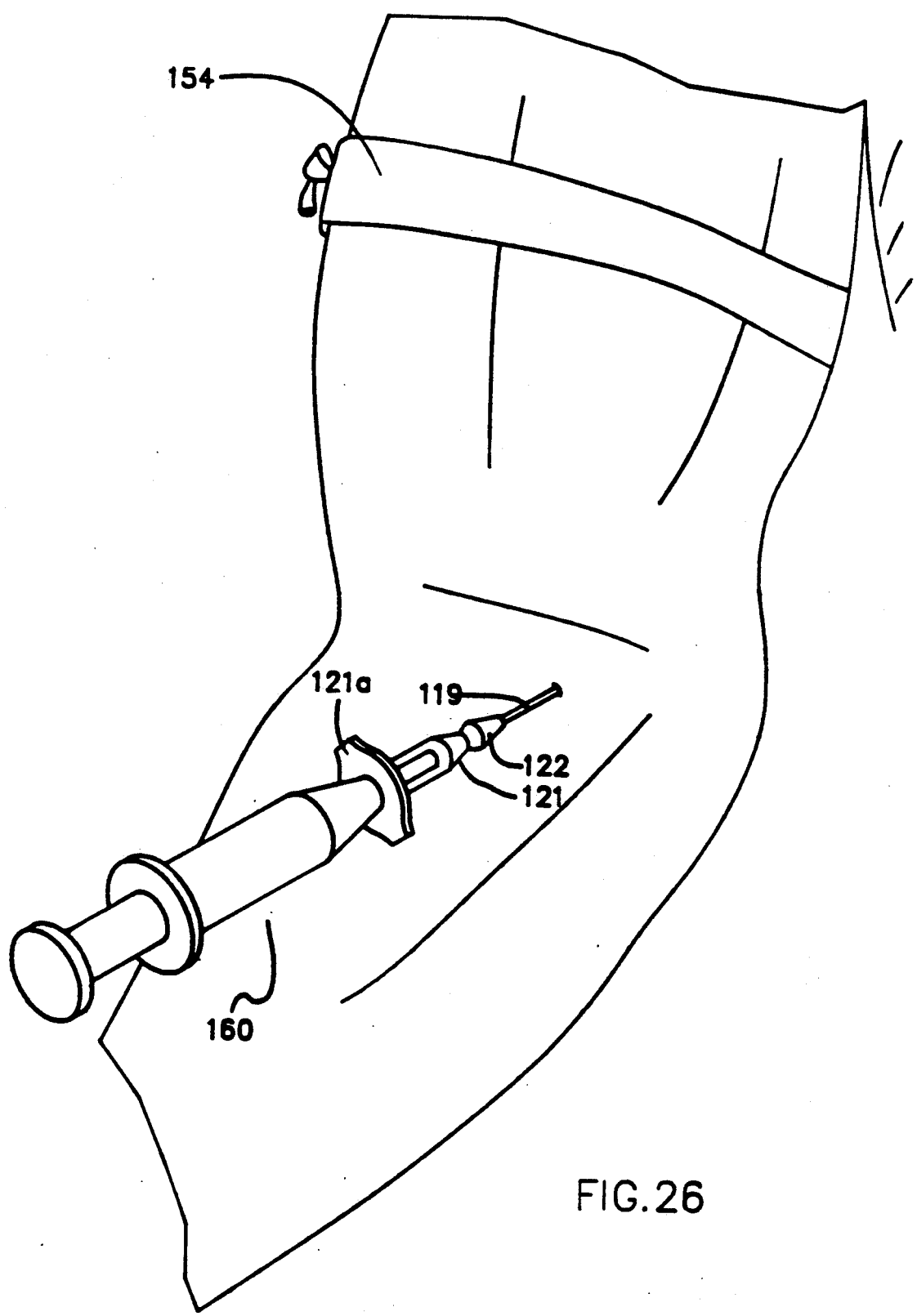
FIG. 26 is a top, perspective view of subsequent use of the implanted cannula device shown in FIG. 25 in connection with a syringe.

Use of the angiocath device of FIGS. 16 et seq. is specifically illustrated in FIGS. 24–26. Thus, the device as shown in FIGS. 16 and 20 is initially inserted into a vein 150 in a patient's arm 152, the vein being more fully revealed by placement of a tourniquet 154 or the like. Upon placement of the needle 103 in the vein 150, the plastic cannula 119 will also extend into the vein along with the needle 103. Subsequent to such placement, a supply of blood can enter hollow needle 103 to fill cavity 117 within the catheter body 107. Subsequently, the needle 103 along with the catheter body 107, which is still in its forward locked position shown in FIG. 20, is removed, along with barrel member 105. This leaves the plastic cannula 119, including the cover portion 121, within the vein 150, in the configuration shown in FIG. 25. Since this is a plastic cannula, it will thus collapse within the vein so as to prevent any further blood from exiting through the cannula 119. In this manner, the device can be subsequently used, such as for injections by hypodermic syringe 160, as shown in FIG. 26. The needle on the front end of hypodermic syringe 160 can thus slide easily within the plastic cannula 119 and enter the vein for the insertion of drugs or other medication, or for the removal of blood, as is required for any particular medical procedure. The cannula 119 can also be used for the hook-up of a conventional intravenous device, or other such known devices. This can thus be done without the need to continuously create new entrance apertures during each such procedure, etc.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A protective catheter device comprising needle means, barrel means for housing said needle means, said needle means being slidably retained within said barrel means for slidable movement from a protected position entirely within said barrel means to an extended position with said needle means extending from said barrel means, whereby said needle means may be inserted into a patient, and positionable locking means for controlling said position of said needle means within said barrel means, said positionable locking means having at least two positions including a first fixed position in which said needle means is freely slidable within said barrel means without interference by said positionable locking means and a second fixed position in which said needle means is locked in said protected position within said barrel means by said positionable locking means by moving said positionable locking means out of said second fixed position.

2. The protective catheter device of claim 1 wherein said needle means includes a needle housing slidably disposed within said barrel member and a needle mounted on said needle housing and projecting therefrom.

3. The protective catheter device of claim 2 wherein said needle housing includes a fluid chamber for receiving fluid from said needle.

4. The protective catheter device of claim 2 wherein said needle housing includes connection means for connecting said needle housing to a tubular conduit for the transport of fluid with respect to said needle housing.

5. The protective catheter device of claim 1 including biasing means for biasing said needle means towards said protected position within said barrel means.

6. The protective catheter device of claim 5 wherein said needle means includes cooperative locking means for cooperating with said positionable locking means whereby when said positionable locking means is in said first fixed position said positionable locking means does not cooperate with said cooperative locking means and when said positionable locking means is in said second fixed position said positionable locking means cooperates with said cooperative locking means to lock said needle means in said, protected position.

7. The protective catheter device of claim 6 wherein said cooperative locking means comprises at least one transverse wall portion of said needle means whereby when said positionable locking means is in said second fixed position, said positionable locking means interacts with said at least one transverse wall portion.

8. The protective catheter device of claim 7 wherein said cooperative locking means comprises a pair of transverse wall portions of said needle means, whereby when said positionable locking means is in said second fixed position said positionable locking means can interact with either one of said pair of transverse wall portions.

9. The protective catheter device of claim 1 wherein said positionable locking means has a third fixed position in which said needle means is locked in said extended position whereby said needle means cannot be displaced from said extended position without repositioning said positionable locking means.

10. The protective catheter device of claim 1 wherein when said positionable locking means is in said second fixed position, said needle means can be locked in either said protected position or said extended position.

11. The protective catheter device of claim 1 wherein said positionable locking means has a third position in which said needle means is slidable from said protected position towards said extended position but is prevented from slidable movement from said extended position towards said protected position.

12. The protective catheter device of claim 1 wherein said positionable locking means comprises pivotable handle means.

13. The protective catheter device of claim 12 wherein said pivotable handle means includes projecting locking arm means, and wherein said barrel means includes at least one aperture for said projecting locking arm means whereby said projecting locking arm means projects into said barrel means through said at least one aperture and when said positionable locking means is in said first position said projecting locking arm means does not engage said needle means and when said positionable locking means is in said second fixed position said projecting locking arm means engages said needle means.

14. The protective catheter device of claim 13 wherein said needle means includes ratchet means and said projecting locking arm means includes pawl means for engaging said ratchet means when said positionable locking means is in said second fixed position.

15. The protective catheter device of claim 14 wherein said positionable locking means has a third position in which said needle means is slidable from said protected position towards said extended position but is prevented from slidable movement from said extended position towards said protected position.

16. The protective catheter device of claim 15 wherein said ratchet means comprises a plurality of teeth, each of said plurality of teeth including a first surface and a second surface, said first surfaced of said plurality of teeth being substantially perpendicular to said needle means and said second surfaced of said plurality of teeth being angularly disposed with respect to said needle means, and wherein said projecting locking arm means includes a first surface and a second surface and wherein said projecting locking arm means is rotatable when said positionable locking means is rotated between said second and third positions whereby when said positionable locking means is in said second position said first surface of said projecting locking arm means engages both said first and second surfaces of said ratchet means, and when said positionable locking means is in said third position said second surface of said projecting locking arm means engages only said first surfaces of said plurality of teeth.

17. The protective catheter device of claim 13 wherein said barrel means includes urging means comprising a raised portion of the surface of said barrel means for urging said positionable locking means away from said at least one aperture when said positionable locking means is in said first position so as to prevent said projecting locking arm means from engaging said needle means.

18. The protective catheter device of claim 17 wherein said projecting locking arm means comprises a pair of projecting locking arms and wherein said barrel means includes a corresponding pair of apertures.

19. The protective catheter device of claim 5 wherein said biasing means comprises spring means disposed within said barrel means and in contact with said needle means.

20. The protective catheter device of claim 19 including core means associated with said spring means for maintaining said spring means in its desired position.

21. The protective catheter device of claim 1 including implantable cannula means mounted on said barrel means whereby when said needle means is in said extended position said needle means projects through said implantable cannula means and said implantable cannula means may be implanted in said patient when said needle means is inserted into said patient.

22. The protective catheter device of claim 21 wherein said implantable cannula means comprises plastic.

23. A protective catheter device comprising needle means, barrel means for housing said needle means, said needle means being slidably retained within said barrel means for slidable movement from a protected position entirely within said barrel means to an extended position with said needle means extending from said barrel means whereby said needle means may be inserted into a patient, positionable locking means for controlling said position of said needle means within said barrel means, said positionable locking means having at least three positions including a first position in which said needle means is freely slidable within said barrel means, a second position in which said needle means is locked in a predetermined position with respect to said barrel means in which the needle means cannot be displaced from said predetermined position without repositioning said positionable locking means, and a third position in which said needle means is slidable from said protected position towards said extended position but is prevented from slidable movement from said extended position towards said protected position, and biasing means for biasing said needle means towards said protected position within said barrel means.

24. The protective catheter device of claim 23 wherein said positionable locking means comprises pivotable handle means.

25. The protective catheter device of claim 24 wherein said pivotable handle means includes projecting locking arm means and wherein said barrel means includes at least one aperture for said projecting locking means whereby said projecting locking arm means projects into said barrel means through said at least one aperture whereby when said positionable locking means is in said first position said projecting locking arm means does not engage said needle means, and when said positionable locking means is in said second position and said third position said positionable locking means engages said needle means.

26. The protective catheter device of claim 25 wherein said needle means includes ratchet means and wherein said projecting locking arm means includes pawl means for engaging said ratchet means when said positionable locking means is in said second and third positions.

27. The protective catheter device of claim 26 wherein said ratchet means comprises a plurality of teeth, each of said plurality of teeth including a first surface and a second surface, said first surfaces of said plurality of teeth being substantially perpendicular to said needle means and said second surfaces of said plurality of teeth being angularly disposed with respect to said needle means, and wherein said projecting locking arm means includes a first surface and a second surface and wherein said projecting locking arm means is rotated when said positionable locking means is rotatable between said second and third positions whereby when said positionable locking means is in said second position said first surface of said projecting locking arm means engages both said first and second surfaces of said ratchet means, and when said positionable locking means is in said third position said second surface of said projecting locking arm means engages only said first surfaces of said plurality of teeth.

28. The protective catheter device of claim 23 wherein said needle means includes a needle housing slidably disposed within said barrel member and a needle mounted on said needle housing and projecting therefrom 29. The protective catheter device of claim 28 wherein said needle housing includes a fluid chamber for receiving fluid from said needle.

30. The protective catheter device of claim 29 wherein said needle housing includes connection means for connecting said needle housing to a tubular conduit for the transport of fluid with respect to said needle housing.

31. The protective catheter device of claim 25 wherein said barrel means includes urging means for urging said positionable locking means away from said at least one aperture when said positionable locking means is in said first position so as to prevent said projecting locking arm means from engaging said needle means.

32. The protective catheter device of claim 31 wherein said projecting locking arm means comprises a pair of projecting locking arms and wherein said barrel means includes a corresponding pair of apertures.

33. The protective catheter device of claim 23 wherein said housing means comprises spring means disposed within said barrel means and in contact with said needle means.

34. A protective catheter device comprising needle means, barrel means for housing said needle means, said needle means being slidably retained within said barrel means for slidable movement from a protected position entirely within said barrel means to an extended position with said needle means extending from said barrel means, whereby said needle means may be inserted into a patient, and positionable locking means for controlling said position of said needle means within said barrel means, said positionable locking means comprising pivotable handle means for controlling said position of said needle means within said barrel means, said pivotable handle means being pivotable between at least two positions including a first position in which said needle means is freely slidable within said barrel means without interference by said positionable locking means and a second position in which said needle means is locked in said protected position within said barrel means, whereby said needle means cannot be displaced from said protected position without repositioning said pivotable handle means.

35. The protective catheter device of claim 34 wherein said needle means includes a needle housing slidably disposed within said barrel member and a needle mounted on said needle housing and projecting therefrom.

36. The protective catheter device of claim 34 including biasing means for biasing said needle means towards said protected position within said barrel means.

37. The protective catheter device of claim 34 wherein said positionable locking means has a third position in which said needle means is locked in said extended position by said positionable locking means whereby said needle means cannot be displaced from said extended position without repositioning said positionable locking means.

38. The protective catheter device of claim 34 wherein said positionable locking means has a third position in which said needle means is slidable from said protected position towards said extended position but is prevented from slidable movement from said extended position towards said protected position by said positionable locking means.

39. The protective catheter device of claim 34 wherein said pivotable handle means includes projecting locking arm means, and wherein said barrel means includes at least one aperture for said projecting locking arm means whereby said projecting locking arm means projects into said barrel means through said at least one aperture and when said positionable locking means is in said first position said projecting locking arm means does not engage said needle means and when said positionable locking means is in said second position said projecting locking arm means engages said needle means.

40. The protective catheter device of claim 39 wherein said needle means includes ratchet means and said projecting locking arm means includes pawl means for engaging said ratchet means when said positionable locking means is in said second position.

41. The protective catheter device of claim 40 wherein said positionable locking means has a third position in which said needle means is slidable from said protected position towards said extended position but is prevented from slidable movement from said extended position towards said protected position.

42. The protective catheter device of claim 41 wherein said ratchet means comprises a plurality of teeth, each of said plurality of teeth including a first surface and a second surface, said first surfaced of said plurality of teeth being substantially perpendicular to said needle means and said second surfaced of said plurality of teeth being angularly disposed with respect to said needle means, and wherein said projecting locking arm means includes a first surface and a second surface and wherein said projecting locking arm means is rotatable when said positionable locking means is rotated between said second and third positions whereby when said positionable locking means is in said second position said first surface of said projecting locking arm means engages both said first and second surfaces of said ratchet means, and when said positionable locking means is in said third position said second surface of said projecting locking arm means engages only said first surfaces of said plurality of teeth.

43. The protective catheter device of claim 34 including implantable cannula means mounted on said barrel means whereby said needle means is in said extended position said needle means projects through said implantable cannula means and said implantable cannula means may be implanted in said patient when said needle means is inserted into said patient.

* * * * *

UNITED STATES PATENT AND TRADEMARK OFFICE
CERTIFICATE OF CORRECTION

PATENT NO. : 5,135,505
DATED : August 4, 1992
INVENTOR(S) : PROTECTIVE CATHETER DEVICE It is certified that error appears in the above-identified patent and that said Letters Patent is hereby corrected as shown below:

```
Column 4, line 33, delete "!" and insert therefor --1--.
Column 4, line 51, delete "!2" and insert therefor --12--.
Column 5, line 30, after "device" insert --1--.
Column 6, line 38, delete "10".
Column 6, line 63, "15ain" should read --15a in".
Column 7, line 19, after "therefrom" insert --.--.
Column 10, line 18, after "necessary" insert --.--.
Column 12, line 41, after means (second occurrence) insert
          --whereby said needle means cannot be displaced from
          said protected position without repositioning said
          positionable locking means--.
Column 13, line 40, after "first" insert --fixed--.
Column 14, line 12, after "position" insert --by interfering
          with said positionable locking means--.
```

Signed and Sealed this

Seventh Day of September, 1993

Attest:

BRUCE LEHMAN

Attesting Officer

Commissioner of Patents and Trademarks